(12) United States Patent
Licamele et al.

(10) Patent No.: US 8,341,877 B2
(45) Date of Patent: Jan. 1, 2013

(54) OPERATION AND CONTROL OF V-TROUGH PHOTOBIOREACTOR SYSTEMS

(75) Inventors: Jason D. Licamele, Scottsdale, AZ (US); Carl L. White, Gilbert, AZ (US)

(73) Assignee: Heliae Development, LLC, Gilbert, AZ (US)

( * ) Notice: Subject to any disclaimer, the term of this patent is extended or adjusted under 35 U.S.C. 154(b) by 0 days.

(21) Appl. No.: 13/249,426

(22) Filed: Sep. 30, 2011

(65) Prior Publication Data

US 2012/0064508 A1   Mar. 15, 2012

Related U.S. Application Data

(63) Continuation of application No. 13/149,463, filed on May 31, 2011.

(51) Int. Cl.
*A01G 7/02* (2006.01)
(52) U.S. Cl. .......................................................... 47/1.4
(58) Field of Classification Search ................... 47/1.4; 435/292.1
See application file for complete search history.

(56) References Cited

U.S. PATENT DOCUMENTS

| | | | |
|---|---|---|---|
| 339,694 A | 4/1886 | Rine | |
| 1,689,277 A | 10/1928 | Burns | |
| 1,790,385 A | 1/1931 | Lorcher | |
| 3,850,802 A | 11/1974 | Berger | |
| 3,850,807 A | 11/1974 | Jones | |
| D244,624 S | 6/1977 | Braid | |
| 4,062,882 A | 12/1977 | Sen Gupta | |
| 4,190,538 A | 2/1980 | Chen | |
| D256,683 S | 9/1980 | Merritt | |
| 4,253,418 A * | 3/1981 | Lockwood et al. | 119/236 |
| 4,264,452 A | 4/1981 | Chen | |
| D271,955 S | 12/1983 | Neil | |
| D286,929 S | 11/1986 | Brandon | |
| 4,787,981 A | 11/1988 | Tanahashi et al. | |
| 4,925,557 A | 5/1990 | Ahlberg, Jr. et al. | |
| D312,983 S | 12/1990 | Powell | |
| 5,014,115 A | 5/1991 | Moser | |
| 5,130,242 A | 7/1992 | Barclay | |
| 5,198,111 A | 3/1993 | Davis | |
| D338,428 S | 8/1993 | Grosfillex | |
| 5,320,963 A * | 6/1994 | Knaack et al. | 435/295.1 |
| 5,338,673 A | 8/1994 | Thepenier et al. | |
| 5,353,745 A | 10/1994 | Fahs, II | |

(Continued)

FOREIGN PATENT DOCUMENTS

CA          2 249 103          4/1999

(Continued)

OTHER PUBLICATIONS

"Algae Oil Extraction," Diversified Technologies, Inc., Bioscience Technology, Jan. 3, 2011 New Source Web Content—US.

(Continued)

*Primary Examiner* — Frank T Palo
(74) *Attorney, Agent, or Firm* — Tom Gallegos, Esq.; Justin Kniep, Esq.; Colleen Superko, Esq.

(57) ABSTRACT

Disclosed herein are photobioreactor systems for high productivity aquaculture or aquafarming for growing of algae or other organisms in an aquatic environment featuring aspects that favor improved growth rates by achieving control over the contents of the growth medium, including carbon source, nitrogen source, and essential trace elements necessary for growth.

16 Claims, 7 Drawing Sheets

U.S. PATENT DOCUMENTS

| | | | |
|---|---|---|---|
| 5,374,657 A | 12/1994 | Kyle | |
| 5,440,028 A | 8/1995 | Buchholz et al. | |
| 5,447,629 A * | 9/1995 | Chaumont et al. | 210/96.1 |
| D364,253 S | 11/1995 | Pianella | |
| 5,539,133 A | 7/1996 | Kohn et al. | |
| 5,545,329 A | 8/1996 | LaMonica | |
| 5,569,383 A | 10/1996 | Vander Ark, Jr. et al. | |
| 5,658,767 A | 8/1997 | Kyle | |
| D384,908 S | 10/1997 | Tuttle | |
| 5,715,773 A | 2/1998 | Martelius | |
| 5,804,072 A | 9/1998 | Yang | |
| D403,268 S | 12/1998 | Dignam | |
| 5,846,816 A * | 12/1998 | Forth | 435/292.1 |
| D413,261 S | 8/1999 | Yerich | |
| 6,024,050 A | 2/2000 | Rheault | |
| D424,893 S | 5/2000 | Goslin et al. | |
| 6,166,231 A | 12/2000 | Hoeksema | |
| 6,192,833 B1 | 2/2001 | Brune et al. | |
| 6,245,555 B1 * | 6/2001 | Curtis | 435/289.1 |
| 6,267,879 B1 | 7/2001 | Gil | |
| 6,372,460 B1 | 4/2002 | Gladue et al. | |
| 6,441,208 B2 | 8/2002 | Bijl et al. | |
| 6,443,312 B1 | 9/2002 | Racine | |
| 6,524,486 B2 | 2/2003 | Borodyanski et al. | |
| 6,579,714 B1 | 6/2003 | Hirabayashi et al. | |
| 6,691,642 B2 | 2/2004 | Dollahan | |
| 6,750,048 B2 | 6/2004 | Ruecker et al. | |
| 6,861,004 B2 | 3/2005 | Benenson, Jr. et al. | |
| 7,001,505 B2 | 2/2006 | Hersh | |
| 7,069,875 B2 | 7/2006 | Warecki | |
| D532,143 S | 11/2006 | Woertler | |
| 7,148,366 B2 | 12/2006 | Cheryan | |
| D561,963 S | 2/2008 | Pedros | |
| 7,661,389 B2 | 2/2010 | Tuerk | |
| 7,678,931 B2 | 3/2010 | Fichtali et al. | |
| 7,690,330 B2 | 4/2010 | Miller | |
| 7,695,626 B2 | 4/2010 | Dueppen et al. | |
| 7,785,479 B1 | 8/2010 | Hosford | |
| 7,816,570 B2 | 10/2010 | Roberts, IV et al. | |
| 7,868,195 B2 | 1/2011 | Fleischer et al. | |
| D643,647 S | 8/2011 | Owen et al. | |
| 7,992,522 B2 | 8/2011 | Harrison et al. | |
| 7,997,025 B1 | 8/2011 | Masse | |
| D661,164 S * | 6/2012 | Licamele | D8/1 |
| 2002/0009493 A1 | 1/2002 | Schwendeman et al. | |
| 2004/0131580 A1 | 7/2004 | Hagino et al. | |
| 2005/0161392 A1 | 7/2005 | Duby | |
| 2005/0164192 A1 | 7/2005 | Graham et al. | |
| 2005/0170479 A1 | 8/2005 | Weaver et al. | |
| 2006/0122410 A1 | 6/2006 | Fichtali et al. | |
| 2007/0025976 A1 | 2/2007 | Kluetz et al. | |
| 2008/0038290 A1 | 2/2008 | Renimel et al. | |
| 2008/0118964 A1 | 5/2008 | Huntley et al. | |
| 2008/0155888 A1 | 7/2008 | Vick et al. | |
| 2008/0160593 A1 | 7/2008 | Oyler | |
| 2008/0311649 A1 | 12/2008 | Cloud et al. | |
| 2009/0029445 A1 | 1/2009 | Eckelberry et al. | |
| 2009/0148918 A1 | 6/2009 | Trimbur et al. | |
| 2009/0148931 A1 | 6/2009 | Wilkerson et al. | |
| 2009/0162919 A1 | 6/2009 | Radaelli et al. | |
| 2009/0181463 A1 | 7/2009 | Chen | |
| 2009/0215155 A1 * | 8/2009 | Cloud et al. | 435/257.1 |
| 2009/0234146 A1 | 9/2009 | Cooney et al. | |
| 2010/0055741 A1 | 3/2010 | Galvez, III et al. | |
| 2010/0068772 A1 | 3/2010 | Downey | |
| 2010/0167381 A1 * | 7/2010 | Woerlee et al. | 435/257.1 |
| 2010/0170149 A1 | 7/2010 | Keeler et al. | |
| 2010/0233761 A1 | 9/2010 | Czartoski et al. | |
| 2010/0261922 A1 | 10/2010 | Fleischer et al. | |
| 2010/0317088 A1 | 12/2010 | Radaelli et al. | |
| 2011/0023360 A1 | 2/2011 | Ryan et al. | |
| 2011/0076747 A1 | 3/2011 | Cloud et al. | |
| 2011/0086386 A1 | 4/2011 | Czartoski et al. | |
| 2011/0124034 A1 | 5/2011 | Kuehnle et al. | |
| 2011/0192073 A1 | 8/2011 | Kale | |
| 2011/0192075 A1 | 8/2011 | Kale | |
| 2011/0195085 A1 | 8/2011 | Kale | |
| 2011/0195484 A1 | 8/2011 | Kale | |
| 2011/0195485 A1 | 8/2011 | Kale | |
| 2011/0196131 A1 | 8/2011 | Kale | |
| 2011/0196132 A1 | 8/2011 | Kale | |
| 2011/0196135 A1 | 8/2011 | Kale | |
| 2011/0258920 A1 | 10/2011 | Licamele et al. | |
| 2011/0258926 A1 | 10/2011 | Bijl | |
| 2012/0064508 A1 * | 3/2012 | Licamele et al. | 435/3 |

FOREIGN PATENT DOCUMENTS

| | | | |
|---|---|---|---|
| EP | 0599711 A1 | 6/1994 | |
| EP | 1 057 833 A1 | 12/2000 | |
| EP | 1 920 777 A1 | 5/2008 | |
| EP | 2 030 626 A1 | 3/2009 | |
| WO | WO-2006/095964 A1 | 9/2006 | |
| WO | WO-2008/031092 A3 | 3/2008 | |
| WO | WO-2008/060571 A2 | 5/2008 | |
| WO | WO-2008/079724 A2 | 7/2008 | |
| WO | WO-2008/144583 A1 | 11/2008 | |
| WO | WO-2009/082696 A1 | 7/2009 | |
| WO | WO-2009/158658 A2 | 12/2009 | |
| WO | WO-2010/002745 A1 | 1/2010 | |
| WO | WO-2010/017002 A1 | 2/2010 | |
| WO | WO-2010/036334 A1 | 4/2010 | |
| WO | WO-2010/120939 A2 | 10/2010 | |
| WO | WO-2010/123903 A1 | 10/2010 | |
| WO | WO-2010/132414 A1 | 11/2010 | |
| WO | WO-2010/138571 A1 | 12/2010 | |
| WO | WO-2010/138620 A1 | 12/2010 | |
| WO | WO-2010/151606 A1 | 12/2010 | |
| WO | WO-2011/036517 A1 | 3/2011 | |
| WO | WO-2011/050472 A1 | 5/2011 | |
| WO | WO-2011/078773 A1 | 6/2011 | |

OTHER PUBLICATIONS

Abu-Rezq, T.S. et al. "Optimum production conditions for different high-quality marine algae," Hydrobiologia, 403: 97-107, 1999.

Agboola, S. et al., "Characterisation and functional properties of Australian rice protein isolates," Journal of Cereal Science 41 (2005) 283-290.

Amin, S. "Review on biofuel oil and gas production processes from microalgae," Energy Conversion and Management 50 (2009) 1834-1840.

Barbosa, M.J.G.V. "Microalgal photobioreactors: Scale-up and optimisation," Ph.D. Thesis, Wageningen University, Wageningen, The Netherlands, 2003.

Benson, B.C. et al., "Optimization of the lighting system for a Hydraulically Integrated Serial Turbidostat Algal Reactor (HISTAR): Economic implications," Aquacultural Engineering 40 (2009) 45-53.

Berberoglu, H. et al., "Radiation characteristics of *Chlamydomonas reinhardtii* CC125 and its truncated chlorophyll antenna transformants tla1, tlaX and tla1-CW$^{+}$" International Journal of Hydrogen Energy 33 (2008) 6467-6483.

Bitog, J.P. et al., "Application of computational fluid dynamics for modeling and designing photobioreactors for microalgae production: A review," Computers and Electronics in Agriculture 76 (2011) 131-147.

Bligh, E.G. et al., "A Rapid Method of Total Lipid Extraction and Purification," Canadian Journal of Biochemistry and Physiology, vol. 37, Aug. 1959, No. 8, pp. 911-917.

Borowitzka, M.A. "Commercial production of microalgae: ponds, tanks, tubes and ferments," Journal of Biotechnology 70 (1999) 313-321.

Bosma, R. et al. "Ultrasound, a new separation technique to harvest microalgae," Journal of Applied Phycology 15: 143-153, 2003.

Brennnan, L. et al., "Biofuels from microalgae—A review of technologies for production, processing, and extractions of biofuels and co-products," Renewable and Sustainable Energy Reviews 14 (2010) 557-577.

Camacho. F.G. et al., "Photobioreactor scale-up for a shear-sensitive dinoflagellate microalga," Process Biochemistry 46 (2011) 936-944.

Catchpole, O.J. et al. "The extraction and fractionation of specialty lipids using near critical fluids," J. of Supercritical Fluids 47 (2009) 591-597.

Chisti, M.Y. et al., "Gas Holdup in Pneumatic Reactors," The Chemical Engineering Journal, 38 (1988) 149-152.
Chisti, Y. "Biodiesel from microalgae," Biotechnology Advances 25 (2007) 294-306.
Christie, W.W., Lipid Analysis, 3rd ed., Oily Press, Bridgewater, UK, 2003, pp. 97-102.
Communication Relating to the Results of the Partial International Search for corresponding International Patent Application No. PCT/US2011/031412 mailed Aug. 9, 2011.
International Search Report and Written Opinion for International Patent Application No. PCT/US2011/031404 mailed Aug. 3, 2011.
International Search Report and Written Opinion for International Patent Application No. PCT/US2011/031407 mailed Aug. 9, 2011.
International Search Report and Written Opinion for International Patent Application No. PCT/US2011/031408 mailed Aug. 9, 2011.
International Search Report and Written Opinion for International Patent Application No. PCT/US2011/031414 mailed Aug. 5, 2011.
International Search Report and Written Opinion for International Patent Application No. PCT/US2011/031417 mailed Aug. 3, 2011.
International Search Report and Written Opinion for International Patent Application No. PCT/US2011/031419 mailed Sep. 5, 2011.
International Search Report and Written Opinion for International Patent Application No. PCT/US2011/031421 mailed Aug. 3, 2011.
U.S. Appl. No. 13/116,602, filed May 26, 2011.
U.S. Appl. No. 13/116,610, filed May 26, 2011.
U.S. Appl. No. 13/149,524, filed May 31, 2011.
U.S. Appl. No. 13/149,531, filed May 31, 2011.
U.S. Appl. No. 13/149,595, filed May 31, 2011.
Csogor, Z. et al., "Light distribution in a novel photobioreactor—modelling for optimization," Journal of Applied Phycology 13: 325-333, 2001.
Daigger, G.T. et al., "Are Membrane Bioreactors Ready for Widespread Application?" Environmental Sciene & Technology, Oct. 1, 2005, pp. 399A-406A.
Database WPI, Week 200326, Thomson Scientific, London, GB; AN 2003-259841 & JP 2002 220402 A (Oriental Bio KK) Aug. 9, 2002, abstract.
De Morais Coutinho, C. et al., "State of art of the application of membrane technology to vegetable oils: A review," Food Research International 42 (2009) 536-550.
Doucha, J. et al., "Outdoor open thin-layer microalgal photobioreactor: potential productivity," J. Appl. Phycol (2009) 21:111-117.
Fabregas. J. et al., "The cell composition of *Nannochloropsis* sp. changes under different irradiances in semicontinuous culture," World Journal of Microbiology & Biotechnology 20, 31-35, 2004.
Forjan, E. et al., "Enhancement of carotenoid production in *Nannochloropsis* by phosphate and sulphur limitation," Communicating Current Research and Educational Topics and Trends in Applied Microbiology, A. Mendez-Vilas (Ed.), 2007, 356-364.
Ghosh, T.K. et al., "Effect of Fractional Gas hold-up ($\epsilon G$) on Volumetric Mass Transfer Co-efficient (KLa) in Modified Airlift Contactor," International Journal of Advanced Science and Technology, vol. 16, Mar. 2010, 21-30.
Grima, E.M. et al., "Recovery of microalgal biomass and metabolites: process options and economics," Biotechnology Advances 20 (2003) 491-515.
Grobbelaar, J.U. "Physiological and technological considerations for optimising mass algal cultures," Journal of Applied Phycology, 12: 201-206, 2000.
Grobbelaar, J.U. et al., "Use of photoacclimation in the design of a novel photobioreactor to achieve high yields in algal mass cultivation," Journal of Applied Phycology 15: 121-126, 2003.
Harun, R. et al., "Bioprocess engineering of microlagae to produce a variety of consumer products," Renewable and Sustainable Energy Reviews 14 (2010) 1037-1047.
Hegde, A. "Development of a Biomass Transducer for Automated Microalgal Bioreactors," A Thesis Submitted to the Graduate Faculty of the Louisiana State University and Agricultural and Mechanical College in partual fulfillment of the requirements for the degree of Master of Science in Engineering Science in The Department of Civil and Environment Engineering, May 2007.
Hejazi, M.A. et al., "Milking of microalgae," Trends in Biotechnology vol. 22, No. 4, Apr. 2004, pp. 189-194.

Herfindal, L. et al., "A high proportion of Baltic Sea benthic cynaobacterial isolates contain apoptogens able to induce rapid death of isolated rat hepatocytes," Toxicon 46 (2005) 252-260.
Herrero, M. et al., "Sub- and supercritical fluid extraction of functional ingredients from different natural sources: Plants, food-by-products, algae and microalgae—A Review," Food Chemistry 98 (2006) 136-148.
Hsieh, C.H. et al., "A novel photobioreactor with transparent rectangular chambers for cultivation of microalgae," Biochemical Engineering Journal 46 (2009) 300-305.
Huang, G. et al., "Biodiesel production by microalgal biotechnology," Applied Energy 87 (2010) 38-46.
Huang, G. et al., "Rapid screening method for lipid production in alga based on Nile red fluorescence," Biomass and Bioenergy 33 (2009) 1386-1392.
Hulatt, C.J. et al., "Energy efficiency of an outdoor microalgal photobioreactor sited at mid-temperate latitude," Bioresource Technology 102 (2011) 6687-6695.
Jacob-Lopes, E. et al., "Effect of light cycles (night/day) on $CO_2$ fixation and biomass production by microalgae in photobioreactors," Chemical Engineering and Processing 48 (2009) 306-310.
James, S.C. et al., "Modeling Algae Growth in an Open-Channel Raceway," Journal of Computational Biology, vol. 17, No. 7, 2010, pp. 895-906.
Ju, Z.Y. et al., "Extraction, Denaturation and Hydrophobic Properties of Rice Flour Proteins," Journal of Food Science, vol. 66, No. 2, 2001, pp. 229-232.
Knuckey, R.M. et al., "Production of microalgal concentrates by flocculation and their assessment as aquaculture feeds," Aquaculural Engineering 35 (2006) 300-313.
Kommareddy, A. et al., "Study of Light as a parameter in the growth of algae in a Photo-Bio Reactor (PBR)," Written for presentation at the 2003 ASAE Annual International Meeting Sponsoted by ASAE, Riviera Hotel and Convention Center, Las Vegas, NV, USA, Jul. 27-30, 2003.
Koris, A. et al., "Dry degumming of vegetable oils by membrane filtration," Desalination 148 (2002) 149-153.
Kumari, P. et al., "Tropical marine macroalgae as potential sources of nutritionally important PUFAs," Food Chemistry 120 (2010) 749-757.
Lee, M. et al., "Isolation and Characterization of a Xanthophyll Aberrant Mutant of the Green Alga Nannochloropsis oculata," Marine Biotechnology, 2006, pp. 238-245.
Lee, Y.K. "Microalgal mass culture systems and methods: Their limitation and potential," Journal of Applied Phycology 13: 307-315, 2011.
Maor, T. et al., "Horizontal Tubular Microalgae Photobioreactor Plant View Factors and Diffuse Radiation," Journal of Solar Energy Engineering, May 2011, vol. 133, 024503-1-7.
Maor, T. et al., "Solar Radiation on Horizontal Tubular Microalgae Photobioreactor: Direct Beam Radiation," Journal of Solar Energy Engineering, May 2011, vol. 133, 024502-1-5.
Marxen, K. et al., "A photobioreactor system for computer controlled cultivation of microalgae," Journal of Applied Phycology (2005) 17: 535-549.
Mata, T.M. et al., "Microalgae for biodiesel production and other applications: A review," Renewable and Sustainable Energy Reviews 14 (2010) 217-232.
Mata, Teresa M. et al., "Microalgae for biodiesel production and other applications: A review," Renewable and Sustainable Energy Reviews (2009), 16 pages.
Mercer, P. et al., "Developments in oil extraction from microalgae," Eur. J. Lipid Sci. Technol. 2011, 113, 539-547.
Pal, D. et al., "The effect of light, salinity, and nitrogen availability on lipid production by *Nannochloropsis* sp.," Appl. Microbiol Biotechnol (2011) 90:1429-1441.
Picture located at http://www.univervegroup.com/image/process5.jpg; website last updated Oct. 10, 2010; first downloaded on May 17, 2011.
Plaza, M. et al., "Screening for bioactive compounds from algae," Journal of Pharmaceuticals and Biomedical Analysis 51 (2010) 450-455.

Ramirez, A. et al., "Lipid extraction from the microalga *Phaeodactylum tricornutum*," Eur. J. Lipid. Technol. 109 (2007) 120-126.

Ranjbar, R. et al., "High Efficiency Production of Astaxanthin in an Airlift Photobioreactor," Journal of Bioscience and Bioengineering, vol. 106, No. 2, 204-207, 2008.

Raynie, D.E., "Modern Extraction Techniques," Anal. Chem. 2006, 78, 3997-4003.

Reyna-Velarde, R. et al., "Hydrodynamic and mass transfer characterization of a flat-panel airlift photobioreactor with high light path," Chemical Engineering and Processing: Process Intensification, Chemical Engineering and Processing 49 (2010) 97-103.

Rhodes, C.J. "Oil from algae; salvation from peak oil?" Science Progress (2009), 92(1), 39-90.

Rittmann, B.E. "Opportunities for Renewable Bioenergy Using Microorganisms," Biotechnology and Bioengineering, vol. 100, No. 2, Jun. 1, 2008, pp. 203-212.

Rittmann, B.E. et al., Environmental Biotechnology: Principles and Applications. McGraw-Hill Book Co., New York, pp. 24-34, 45, 57, 353-378, (2001).

Rocha. J.M.S. et al., "Growth aspects of the marine microalga *Nannochloropsis gaditana*," Biomolecular Engineering 20 (2003) 237-242.

Rossignol, N. et al., "Membrane technology for the continuous separation microalgae/culture medium: compared performances of cross-flow microfiltration and ultrafiltration," Aquacultutal Engineering 20 (1999) 191-208.

Rusch, K.A. et al., "The hydraulically integrated serial turbidostat algal reactor (HISTAR) for microalgal production," Aquacultural Engineering 27 (2003) 249-264.

Sato, T. et al., "Development of virtual photobioreactor for microalgae culture considering turbulent flow and flashing light effect," Energy Conversion and Management 51 (2010) 1196-1201.

Sato, T. et al., "Invention of outdoor closed type photobioreactor for microalgae," Energy Conversion and Management 47 (2006) 791-799.

Schaper, R. et al., "Temperature Effects on the Gas Hold-Up in Agitated Vessels," 2002, pp. 1-9.

Sierra. E. et al., "Characterization of a flat plate photobioreactor for the production of microalgae," Chemical Engineering Journal 138 (2008) 136-147.

Slegers, P.M. et al., "Design scenarios for flat panel photobioreactors," Applied Energy 88 (2011) 3342-3353.

Spolaore, P. et al. "Commercial Applications of Microalgae," Journal of Bioscience and Bioengineering, vol. 101, No. 2, 87-96, 2006.

Steinitz, Y. et al., "A Mutant of the Cyanobacterium Plectonema Boryanum Resistant to Photooxidation," Plant Science Letters, vol. 16, Issues 2-3, p. 327-335, Oct. 1979.

Su, Z. et al. "Study on the destabilization mixing in the flat plate photobioreactor by means of CFD," Biomass and Bioenergy 34 (2010) 1879-1884.

Tamburic, B. et al., "Design of a novel flat-plate photobioreactor system for green algal hydrogen production," International Journal of Hydrogen Energy 36 (2011) 6578-6591.

Uduman, N. et al. "Dewatering of microalgal cultures: A major bottleneck to algae-based fuels," Journal of Renewable and Sustainable Energy 2, 2010, 012701-1-012701-15.

Uduman, N. et al., "Marine microalgae flocculation and focused beam reflectance measurement," Chemical Engineering Journal 162 (2010) 935-940.

Ugwu, C.U. et al., "Photobioreactors for mass cultivation of algae," Bioresource Technology 99 (2008) 4021-4028.

Voorhees, K.J. et al., "Analysis of Insoluble Carbonaceous Materials from Airborne Particles Collected in Pristine Region of Colorado," Journal of Analytical and Applied Pyrolysis, 18 (1991) 189-205.

Wachowicz, M. et al. "The protein of the alga *Spirulina platensis*. (translated)." Database FSTA [Online] International Food Information Service (IFIS), Frankfurt-Main, DE; 1974.

Webvitamins (2011, updated) "Globulin Protein Concentrate", www.webvitamins.com/Nutrient.aspx?id=2007, p. 1.

Weyer, K.M. et al., "Theorectical Maximum Algal Oil Production," Bioenerg. Res. (2010) 3:204-213.

Wu, X. et al., "Simulation of algae growth in a bench scale internal loop sirlift reactor," Chemical Engineering Science 59 (2004) 2899-2912.

Zhang, C. et al. "Performance of a groove-type photobioreactor for hydrogen production by immobilized photosynthetic bacteria," International Journal of Hydrogen Energy 35 (2010) 5284-5292.

Zhu, C.J. et al. "Determination of biomass dry weight of marine microalgae," Journal of Applied Phycology 9:189-194, 1997.

Zhu, Y.H. et al., "Continuous cultivation of Dunaliella salina in photobioreactor for the production of β-carotene," Eur Food Res Technol (2008) 227:953-959.

Zijffers. J.W. F. et al., "Maximum Photosynthetic Yield of Green Microalgae in Photobioreactors," Mar Biotechnol (2010) 12:708-718.

Zimmerman, W.B. et al., "Design of an airlift loop bioreactor and pilot scales studies with fluidic oscillator induced microbubbles for growth of a microalgae Dunaliella salina," Applied Energy 88 (2011) 3357-3369.

Zittelli, G.C. et al., "A Modular Flat Panel Photobioreactor (MFPP) for indoor mass cultivation of Nannochloropsis," Journal of Applied Phycology 12: 521-526, 2000.

"Cultivation of Algae in Photobioreactor," Oilgae, Oct. 2011, retrieved from http://www.oilgae.com/algae/cult/pbr/pbr.html on Nov. 9, 2011, No Author, 11 pages.

"Industrial Photobioreactor for Microalgae and Photosynthetic Bacteria Massive Cultivation," M2M Engineering, Oct. 2011, retrieved from http://www.m2mengineering.it/index.php?option=com_content&view=article&id=47%3Afotobioreattori-per-colture-massive&catid=51%3Afotobioreattori-industriali&Itemid=77&lang=en, No Author, 4 pages.

"Monitor, Analyze, and Protect the World's Natural Resources,"YSI, Nov. 2011, retrieved from http://www.ysi.com/parameters.php, No Author, 2 pages.

Culturing Solutions, Inc., "Continuous Algae Production," Phyta-Platform, 2011, 3 pages, retrieved from http://www.culturingsolutions.com/Phyta-Platform.html on Oct. 18, 2011, No Author.

Sandnes, et al., "Real-time Monitoring and Automatic Density Control of Large-Scale Microalgal Cultures Using Near Infrared (NIR) Optical Density Sensors," Journal of Biotechnology 122, 2006, pp. 209-215.

* cited by examiner

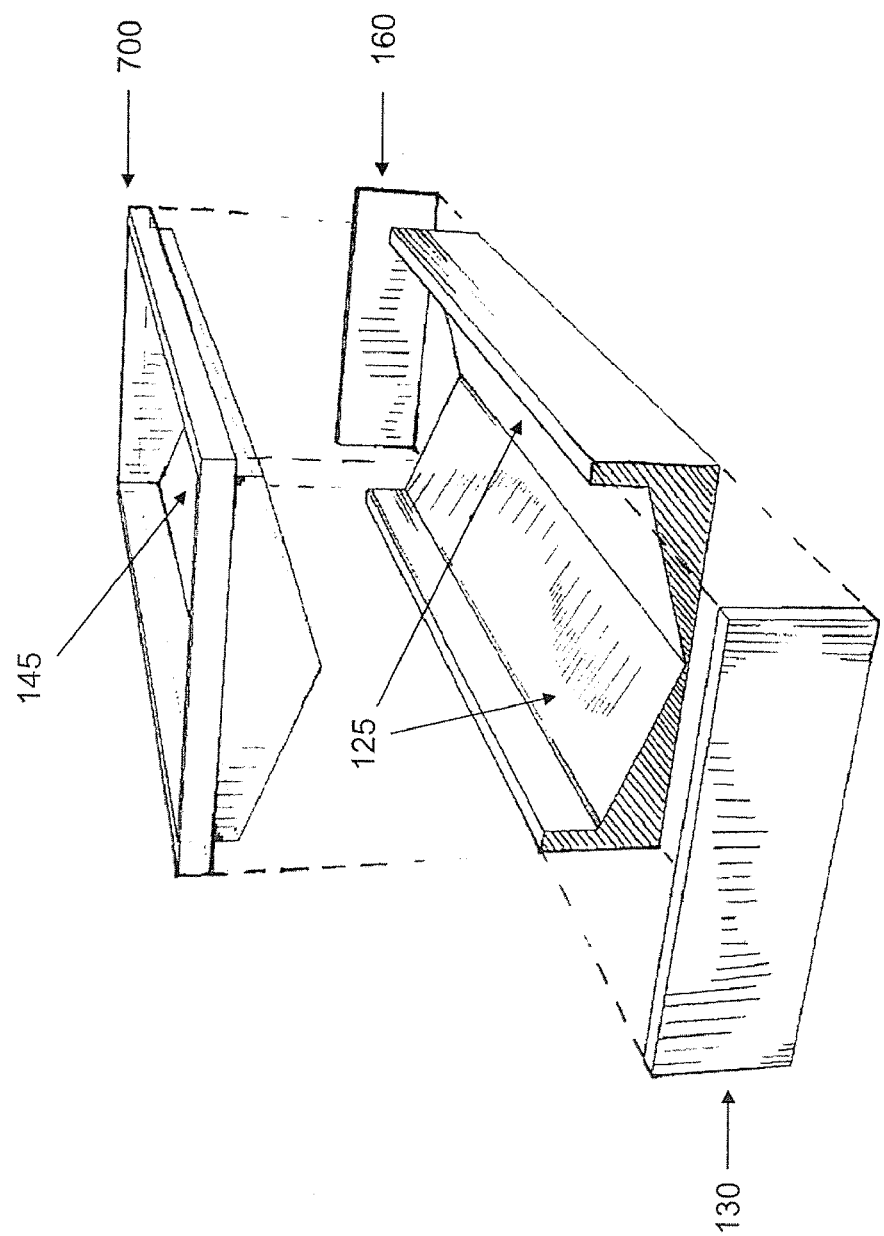

OPERATION AND CONTROL OF V-TROUGH PHOTOBIOREACTOR SYSTEMS

This application is a continuation of and claims the benefit of priority of U.S. patent application Ser. No. 13/149,463, filed May 31, 2011, the contents of which are hereby incorporated by reference in their entirety.

FIELD OF THE INVENTION

Disclosed herein are photobioreactor systems for high productivity aquaculture or aquafarming for growing of algae or other organisms in an aquatic environment featuring aspects that favor improved growth rates by achieving efficient mixing rates, control over the contents of the growth medium, including carbon source, nitrogen source, and essential trace elements necessary for growth.

BACKGROUND

Algae have gained significant importance in recent years given their advantage in solving several critical global issues such as the production of renewable fuels and animal feedstock, reducing global climate change via carbon dioxide remediation, wastewater treatment, and sustainability. Algae farming is also used for the production of food, feed, nutraceuticals, chemicals, biofuels, pharmaceuticals, and other products that can be extracted from algae.

Algae's superiority as a biofuel feedstock arises from a number of factors such as high per-acre productivity when compared to typical terrestrial oil crop plants, non-food based feedstock resources, and its ability to be cultivated on otherwise non-productive, non-arable land.

Several thousand species of algae have been screened and studied for lipid production worldwide over the past several decades, of which about 300 species rich in lipid production have been identified. The lipids produced by algae are similar in composition when compared to other contemporary oil sources such as oil seeds, cereals, and nuts.

As the United States has already consumed over 80% of its proven oil reserves, it currently imports more than 60% of its oil. It is anticipated that within 20 years the United States will be importing in the range of 80-90% of its oil. Much of this imported oil is supplied by nations in politically volatile regions of the world, a fact which poses a constant threat to a stable oil supply for the United States. Although the United States can continue to increasingly import foreign oil, global oil supplies are not infinite and importation continues to increase the United States trade deficit and create an increasing burden on the economy.

Commercial cultivation of lipid-producing algae provides a solution to the growing problem of oil shortages and increases in cost of importation. Algae oil can be used to replace petroleum-based products. Algae can be used to generate oil of varying lipid profiles for use in a variety of applications, including, but not limited to, the generation of diesel, gasoline, kerosene, and jet fuel.

Algae farming typically uses photobioreactors (PBRs), such as flat panel PBRs and tubular PBRs, which are small in volume in order to improve the amount of light utilized by the algae. These devices have high productivity, but not high enough to make up for the loss in volume. Other PBR systems, such as ponds, raceways or troughs are used to provide larger scale production, but these systems suffer from low productivity. Current PBR systems are typically designed with flat bottoms where solids settle out, and over time potentially lead to bacterial and fungal growth. Such unwanted growth potentially decreases the productivity and growth of algae. Additionally, pond systems are large systems (half acre, acre, or hectare size) with minimal mixing. Mixing in these systems is often accomplished by way of paddle wheels or air lines, which are not optimal for algae growth, and do not develop a systematic pattern of mixing within the system to keep solids from settling out. Optimal mixing of such systems require large amounts of energy, reducing overall cost efficiency. Pond or raceway systems also require maintenance such as draining, harvesting, and cleaning to maintain optimal productivity levels for algae growth. This results in downtime of the system, labor to clean, and large amounts of water to refill these systems.

The present disclosure provides V-shaped PBR systems designed for optimal productivity at large volumes in order to deliver a high yield per acre. These systems produces large volumes of algae in a highly productive and cost efficient manner.

BRIEF SUMMARY OF THE INVENTION

In one aspect, a photobioreactor is disclosed which comprises a cavity defined by: a substantially V-shaped base comprising: two base walls, said base walls meeting proximate to an axis defining an interior angle, each base wall comprising: a sloped portion and a substantially vertical portion, a proximal end and a distal end, and a length extending along said axis and a width extending perpendicular to said axis; the cavity being further defined by: a proximal side wall adjacent to said proximal end, and a distal side wall adjacent to said distal end; and the photobioreactor system further comprising: at least one gas delivery system disposed within said cavity and extending parallel to said axis, and at least one carbon dioxide delivery system disposed within said cavity and extending parallel to said axis.

In another aspect, a kit for assembling a photobioreactor is disclosed which comprises two base walls, a proximal side wall, a distal side wall and a first liner capable of being folded, collapsed, or rolled up, which, when assembled into a photobioreactor, comprises a cavity defined by: a substantially V-shaped base comprising: said base walls, said base walls meeting proximate to an axis defining an interior angle, each base wall comprising: a sloped portion and a substantially vertical portion, a proximal end and a distal end, and a length extending along said axis and a width extending perpendicular to said axis; and the cavity being further defined by: said proximal side wall, disposed adjacent to said proximal end, and said distal side wall, disposed adjacent to said distal end.

In another aspect, a method of producing a biomass is disclosed which comprises dispensing a biomass culture medium in a photobioreactor, the photobioreactor comprising: a cavity defined by: a substantially V-shaped base comprising: two base walls, said base walls meeting proximate to an axis defining an interior angle, each base wall comprising: a sloped portion and a substantially vertical portion, a proximal end and a distal end, and a length extending along said axis and a width extending perpendicular to said axis; the cavity being further defined by: a proximal side wall adjacent to said proximal end, and a distal side wall adjacent to said distal end; the photobioreactor system further comprising: at least one gas delivery system disposed within said cavity and extending parallel to said axis, and at least one carbon dioxide delivery system disposed within said cavity and extending parallel to said axis; and the method further comprising supplying a gas through said gas delivery system, producing bubbles having diameters between about 1 and about 3 mm, and supplying carbon dioxide through said carbon dioxide delivery system, producing bubbles having diameters between about 0.001 and about 500 microns.

The V-trough PBR systems disclosed herein concentrate settleable material at an axis, and apply gas at the same point for mixing and keeping materials and algae in suspension. This system of agitation also serves to bring algae to the surface, where light penetration may be focused for increased productivity. The geometric shape of the V defines the axis where solids would otherwise concentrate. These V-trough PBR systems are more efficient and require less energy for mixing because the culture medium is concentrated along the axis at the bottom of the V, creating a specific location where application of agitation is most efficient. This allows the system to be run in a semi-continuous or continuous mode, which decreases downtime, labor and energy that would otherwise be required to keep the system running efficiently, and thus resulting in improved total annual productivity.

GLOSSARY

As used herein, the term "productivity" refers to a standing biomass concentration for a batch harvest, or the daily biomass generated per given volume for a semi-continuously or continuously operated PBR. Productivity is a function of the amount of light, carbon dioxide, and nutrients that the biomaterials receive.

As used herein, the term "light" generally refers to photosynthetically active radiation (PAR). This can come in the form of unseparated wavelengths of light (such as sunlight), or selected wavelengths of light. Light can be natural or supplied by other means, such as light emitting diodes (LEDs).

BRIEF DESCRIPTION OF THE FIGURES

Like numerals indicate like features in the Figures included herein.

FIG. 7 shows an exploded aspected view of an illustrative embodiment of the V-trough PBR systems disclosed herein, where the system is disassembled.

DETAILED DESCRIPTION

Figure 1:
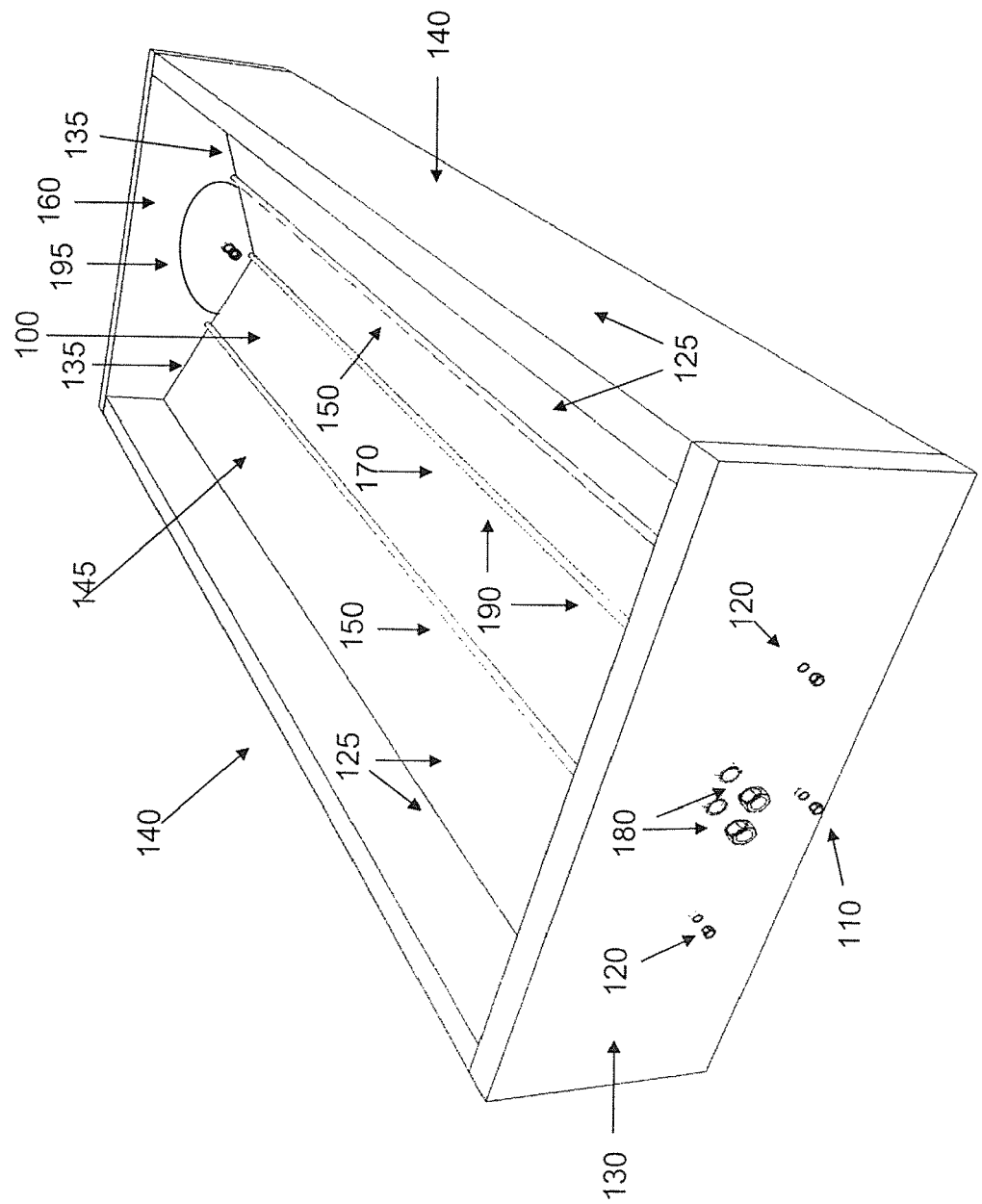
FIG. 1 shows a perspective view schematic of an illustrative embodiment of the V-trough PBR systems disclosed herein.

In one aspect, a photobioreactor is disclosed which comprises a cavity defined by: a substantially V-shaped base comprising: two base walls, said base walls meeting proximate to an axis defining an interior angle, each base wall comprising: a sloped portion and a substantially vertical portion, a proximal end and a distal end, and a length extending along said axis and a width extending perpendicular to said axis; the cavity being further defined by: a proximal side wall adjacent to said proximal end, and a distal side wall adjacent to said distal end; and the photobioreactor system further comprising: at least one gas delivery system disposed within said cavity and extending parallel to said axis, and at least one carbon dioxide delivery system disposed within said cavity and extending parallel to said axis.

In another aspect, a kit for assembling a photobioreactor is disclosed which comprises two base walls, a proximal side wall, a distal side wall and a first liner capable of being folded, collapsed, or rolled up, which, when assembled into a photobioreactor, comprises a cavity defined by: a substantially V-shaped base comprising: said base walls, said base walls meeting proximate to an axis defining an interior angle, each base wall comprising: a sloped portion and a substantially vertical portion, a proximal end and a distal end, and a length extending along said axis and a width extending perpendicular to said axis; and the cavity being further defined by: said proximal side wall, disposed adjacent to said proximal end, and said distal side wall, disposed adjacent to said distal end.

In another aspect, a method of producing a biomass is disclosed which comprises dispensing a biomass culture medium in a photobioreactor, the photobioreactor comprising: a cavity defined by: a substantially V-shaped base comprising: two base walls, said base walls meeting proximate to an axis defining an interior angle, each base wall comprising: a sloped portion and a substantially vertical portion, a proximal end and a distal end, and a length extending along said axis and a width extending perpendicular to said axis; the cavity being further defined by: a proximal side wall adjacent to said proximal end, and a distal side wall adjacent to said distal end; the photobioreactor system further comprising: at least one gas delivery system disposed within said cavity and extending parallel to said axis, and at least one carbon dioxide delivery system disposed within said cavity and extending parallel to said axis; and the method further comprising supplying a gas through said gas delivery system, producing bubbles having diameters between about 1 and about 3 mm, and supplying carbon dioxide through said carbon dioxide delivery system, producing bubbles having diameters between about 0.001 and about 500 microns.

Shape of the V-Trough

The V-shaped base of the V-trough PBR systems disclosed herein comprises an inner dimension that tapers substantially to a V at the bottom. In some embodiments, the bottom of the trough is a point (i.e. meeting of two flat elements). In further embodiments, the bottom of the trough is rounded. This property results in reduced dead space as compared to a flat-bottomed tank, allows for increased mixing rate of the culture medium, improved turnover of the medium and biomass within the PBRs and overall high volume, high productivity PBR systems. Absent this V-shaped base, the propensity of solids to settle at the bottom of the PBR is increased.

The V-shaped base defines an interior angle less than about 180° and more than about 45°. In some embodiments, the angle is between about 34° and about 140°. In some embodiments, the angle is between about 60° and about 140°. In some embodiments, the angle is between about 34° and about 120°. In some embodiments, the angle is between about 60° and about 120°. In some embodiments, the angle is between about 80° and about 112°. In some embodiments, the angle is between about 800° and about 100°. The angle depends on light source, geographic location of the PBR, the targeted biological materials, standing biomaterial concentration, and desired productivity. As the angle decreases, the total volume of the PBR decreases, assuming all other dimensions are held constant. The substantially vertical portions of the base walls can extend vertically to compensate for loss in volume as the angle decreases.

Side walls extend upward from the V-shaped base to increase the total volume of the PBR. As the side walls extend, the volume of the PBR increases while maintaining the same footprint, given that all other dimensions are held constant. In some embodiments, the side walls extend vertically upwards. In some embodiments, the side walls extend upwards at an angle. In some embodiments, the side walls range in thickness from between about 2 to about 10 inches. In further embodiments, the side walls range in thickness from between about 4 to about 6 inches. In some embodiments, the side walls are straight. In further embodiments, the side walls are curved. In some embodiments, the side walls and V-shaped base curve such that they form a single wall, with no discernible separation. In some embodiments, the cavity is a single formed unit.

The desired length and volume of the V-trough PBR systems disclosed herein is determined by the efficiency of heating and/or cooling capacity, and retention time of the biomaterials. The volumes of the systems are designed to harvest biomaterials before growth and productivity drop off as a function of cell longevity and cell vigor. Cell longevity and cell vigor is a function of the nature of the biomaterials, contamination in the culture, environmental parameters applied to the culture, and water chemistry parameters. In some embodiments, the V-trough PBR system is between about 15 feet and about 100 feet long. In further embodiments, the system is over 100 feet long.

The volume of the V-trough PBR systems disclosed herein are determined by a number of factors, including the angle of the V-shaped base, the dimensions of the side walls, and the overall length and width of the V-trough. Generally, for light-dependent biomaterials, productivity is increased as the volume of the PBR system decreases, due to increased mixing and exposure of the biomaterials to light. The V-trough is designed to mitigate the loss in productivity that occurs when the volume of a vessel is increased. The surface area to volume ratio of the V-trough is such that the biomaterials have a greater exposure to light, as biomaterials circulating through the PBR system will receive differing amounts of light depending on whether they are proximate to an illuminated surface or distal from it (in a "dark zone") during circulation.

The reduction of settleable solids in the V-trough PBR systems disclosed herein provides a significant advantage over existing devices. First, the systems disclosed herein can be run in a continuous or semi-continuous mode, while existing devices require downtime and maintenance costs to remove settled solids. Further, because the system does not need to be stopped periodically, or with the frequency of existing systems, the biomass shows an improved probability of surviving at the desired productivity for a longer period of time than existing devices.

Gas Delivery System

The gas delivery systems of the V-trough PBR systems disclosed herein can be used, inter alia, for efficient mixing of the culture medium. The gas delivery systems are placed strategically along or near the axis defined by the bottom of the V to keep solids in suspension, and to provide improved mixing of the culture medium. Mixing rate of the culture medium can be controlled by the gas delivery system alone, or in combination with other agitation means. Control of mixing rate and retention time of the culture medium is important so that these parameters can be varied depending on the concentration of the medium. Rate of gas injection, combined with the V-shaped design drives the mixing efficiency of the system. Generally, for light-dependent biomaterials, a higher rate of mixing is desired to increase the amount of biomaterials coming into contact with the light, resulting in greater productivity. In some embodiments, the gas comprises air. In further embodiments, the gas comprises ozone.

The gas delivery systems disclosed herein can produce gas bubbles of varying size. Bubble size affects several factors relevant to the V-trough PBR systems disclosed herein. First, larger bubbles result in more efficient mixing, while smaller bubbles mix the culture medium less efficiently. Second, larger bubbles have reduced surface area compared to smaller bubbles, resulting in less gas exchange with the culture medium. Larger bubbles thus can have less of an effect on the pH of the system, while smaller bubbles can be utilized for more efficient gas diffusion into the system. In some embodiments, bubble size is controlled by the type of gas delivery system, the pressure of the gas applied, the density of the gas being introduced into the system, and the perforation, pore, injection point, aperture or orifice size through which the gas is introduced into the culture medium. In some embodiments, the bubbles are between about 1 and about 3 mm in diameter. In some embodiments, the bubbles are between about 1 and about 3 mm in diameter, and are used primarily for mixing the culture medium. In further embodiments, the bubbles are less than about 1 mm in diameter (i.e. micro bubbles). In some embodiments, the bubbles are less than about 1 mm in diameter and are used primarily for gas diffusion into the culture medium. In still further embodiments, the bubbles are between about 0.001 and about 500 microns in diameter. In some embodiments, the gas delivery systems operate at a pressure between about 1 and about 50 psi, and generate bubble size of between about 1 and about 3 mm in diameter. In some embodiments, air is applied at a bubble size of about 1 to about 3 mm to aid in mixing the medium.

In some embodiments, the culture medium in the V-trough photobioreactor systems disclosed herein is mixed or circulated by the gas delivery system. In some embodiments, the gas exiting from the gas delivery system generates an upward movement of biomass and liquid phase from the axis towards the top of the system. In some embodiments, the biomass is exposed to light near the top of the circulation or mixing path. In some embodiments, the medium then circulates outwards towards the substantially vertical portions of the base walls, which in some embodiments provides for additional exposure to light. In some embodiments, the culture medium then moves down the base walls and back towards the axis, where the process is repeated continuously or semi-continuously. Further description of this type of circulation is found in U.S. Pat. No. 5,846,816 to Forth, the contents of which are incorporated herein by reference in their entireties.

In some embodiments, the gas delivery system uses positive pressure to prevent infiltration of water and other components into the gas delivery system. In further embodiments, perforation, pore, injection point, aperture or orifice size is selected to prevent infiltration of molecules, such as proteins, having molecular weights less than about 30,000 Daltons.

The gas delivery systems are made of any suitable materials. In some embodiments, the gas delivery systems comprise ceramic, stainless steel, rubber, glass, or polyethylene. In some embodiments, the gas delivery system comprises a line running along the axis of the V-shaped base, perforated with perforations, pores, injection points, apertures or orifices along its length. In some embodiments, the gas delivery system comprises a gas sparging line. In some embodiments, bubbles are sparged into the medium through stainless steel, membrane and other materials having the desired perforation, pore, injection point, aperture or orifice size range. In some embodiments, the gas delivery system comprises a Graver Technologies, Glasgow, Del. sintered metal filter with a 1 micron pore size that is adapted to sparging carbon dioxide into growth medium. In some embodiments, the perforations, pores, injection points, apertures or orifices comprise holes and/or slots. In some embodiments, the holes and/or slots are oriented vertically. In further embodiments, the holes and/or slots are oriented at an angle to improve mixing of the medium. In some embodiments, the holes and/or slots are arranged uniformly along the gas delivery system. In further embodiments, the holes and/or slots are arranged randomly along the gas delivery system. In some embodiments, holes and/or slots are oriented both vertically and at an angle. In some embodiments, the line or lines comprise perforations, pores, injection points, apertures or orifices strategically placed along their length to achieve consistent and congruent pressure along the line for even gas dispersion. In some embodiments, the gas delivery systems comprise micro-pore diffusers. In some embodiments, the perforations, pores, injection points, apertures or orifices comprise gas injection ports.

In some embodiments, a single gas delivery system is present in each V-trough PBR system. In some embodiments, the system comprises a single line perforated with perforations, pores, injection points, apertures or orifices. In further embodiments, the V-trough PBR systems disclosed herein comprise multiple gas delivery systems. In some embodiments, the system comprises an array of lines perforated with perforations, pores, injection points, apertures or orifices. In some embodiments, the gas delivery system comprises at least one terminal through at least a portion of one of the side walls defining the cavity of the V-trough PBR systems disclosed herein.

In some embodiments where ozone is delivered to the V-trough PBR systems disclosed herein, ozone is provided at levels that do not harm the biomass, but kill or inhibit the growth of contaminants or predators. In some embodiments, ozone is delivered by a separate line than other gases. In some embodiments, ozone is delivered by the same line as other gases. In some embodiments, ozone is applied constantly. In further embodiments, ozone is applied prophylactically, to prevent contamination rates reaching detrimental levels in the culture. The amount and timing of the ozone application for sterilization of the culture is determined by the contaminant in question. In some embodiments, ozone is applied at levels between about 0.5 and about 1 mg/L for sterilizing viable cultures without effecting the targeted biomass.

Carbon Dioxide Delivery System

The carbon dioxide delivery systems of the V-trough PBR systems disclosed herein are separated from the gas delivery systems. Carbon dioxide is required for the growth of many culture media, such as algae, and thus serves as a carbon source. The separation of carbon dioxide and gas delivery systems have the advantage over, e.g., a single system which delivers carbon dioxide-enriched air, by being able to optimize mixing and carbon source separately.

The carbon dioxide delivery systems disclosed herein can produce carbon dioxide bubbles of varying size. As with other gasses, carbon dioxide bubble size affects several factors relevant to the V-trough PBR systems disclosed herein. First, carbon dioxide bubbles can contribute to mixing of the system, and, as with other gasses, larger bubbles result in more efficient mixing, while smaller bubbles mix the culture medium less efficiently. Second, smaller carbon dioxide bubbles have increased surface area compared to larger bubbles, resulting in more gas exchange with the culture medium and more efficient delivery of the carbon source to the culture medium. This can also affect the pH of the system.

In some embodiments, bubble size is controlled by the type of gas delivery system, the pressure of the gas applied, the density of the gas being introduced into the system, and the perforation, pore, injection point, aperture or orifice size of the through which the gas is introduced into the culture medium. In some embodiments, the bubbles are between about 1 and about 3 mm in diameter. In some embodiments, the bubbles are between about 1 and about 3 mm in diameter, and are used primarily for mixing the culture medium. In further embodiments, the bubbles are less than about 1 mm in diameter (i.e. micro bubbles). In some embodiments, the bubbles are less than about 1 mm in diameter and are used primarily for gas diffusion into the culture medium. In still further embodiments, the bubbles are between about 0.001 and about 500 microns in diameter for high efficiency gas exchange. In some embodiments, the gas delivery systems operate at a pressure between about 1 and about 50 psi, and generate bubble size of between about 1 and about 3 mm in diameter.

In some embodiments, carbon dioxide is applied at a bubble size of less than about 1 mm for efficient gas exchange for enhancing photosynthesis. In some embodiments, carbon dioxide bubbles are presented in the micron to sub-micron range. For example, the surface area of ten 100 micron diameter bubbles is 1,000 times the surface area of a bubble having a diameter of 1 mm. The result is an exponential increase in dissolved carbon dioxide into the surrounding liquid medium as bubble size reduces.

In some embodiments, carbon dioxide is applied at a rate and bubble size, relative to the concentration of carbon dioxide-consuming biomaterials in the system. In these embodiments, carbon dioxide is supplied relative to the biomass concentration in the system for maximum efficiency. In some embodiments, as the standing biomass concentration increases, the amount of carbon dioxide required for beneficial growth also increases.

In some embodiments, the carbon dioxide delivery systems are disposed adjacent to the gas delivery systems. In further embodiments, the carbon dioxide delivery systems are disposed at a different location. In some embodiments, the carbon dioxide delivery systems are disposed away from the axis to provide additional mixing along the side walls.

In some embodiments, the carbon dioxide delivery system uses positive pressure to prevent infiltration of water and other components into the carbon dioxide delivery system. In further embodiments, perforation, pore, injection point, aperture or orifice size is selected to prevent infiltration of molecules, such as proteins, having molecular weights less than about 30,000 Daltons.

The carbon dioxide delivery systems are made of any suitable materials. In some embodiments, the carbon dioxide delivery system comprises a line running along the axis of the V-shaped base, perforated with perforations, pores, injection points, apertures or orifices distributed along its length. In some embodiments, the gas delivery system comprises a gas sparging line. In some embodiments, bubbles are sparged into the medium through stainless steel, membrane and other materials having the desired perforation, pore, injection point, aperture or orifice size range. In some embodiments, the gas delivery system comprises a Graver Technologies, Glasgow, Del. sintered metal filter with a 1 micron pore size that is adapted to sparging carbon dioxide into growth medium. In some embodiments, the perforations, pores, injection points, apertures or orifices comprise holes and/or slots. In some embodiments, the holes and/or slots are oriented vertically. In further embodiments, the holes and/or slots are oriented at an angle to improve mixing of the medium or more efficient gas dissolution. In some embodiments, the holes and/or slots are arranged uniformly along the carbon dioxide delivery system. In further embodiments, the holes and/or slots are arranged randomly along the carbon dioxide delivery system. In some embodiments, holes and/or slots are oriented both vertically and at an angle. In some embodiments, the line or lines comprise perforations, pores, injection points, apertures or orifices strategically placed along their length to achieve consistent and congruent pressure along the line for even gas dispersion. In some embodiments, the carbon dioxide delivery systems comprise micropore diffusers.

In some embodiments, a single carbon dioxide delivery system is present in each V-trough PBR system. In some embodiments, the system comprises a single line perforated with holes and/or slots. In further embodiments, the V-trough PBR systems disclosed herein comprise multiple sources of carbon dioxide for injection into the culture medium. In some embodiments, the carbon dioxide delivery system comprises one line perforated with holes and/or slots on either side of the gas delivery system. In some embodiments, the system comprises an array of lines perforated with holes and/or slots. In some embodiments, the carbon dioxide delivery system comprises at least one terminal through at least a portion of one of the side walls defining the cavity of the V-trough PBR systems disclosed herein.

The ability to independently change the bubble size of the gas and carbon dioxide delivery systems in the V-trough PBR systems disclosed herein allows for beneficial productivity of the biomass, and represents a significant advantage over existing systems.

pH Stabilizers

As disclosed above, gas and carbon dioxide affect the pH of the system. To customize and stabilize the pH of the system, pH buffers are used. The use of pH stabilizers allows gas to be used at a constant and beneficial flow rate and bubble size for maximum efficiency in mixing, while carbon dioxide is used at a constant and beneficial flow rate and bubble size to provide maximum efficiency in supplying a carbon source to the system, without the need to vary these parameters to affect the pH.

In some embodiments, the biomaterials in the V-trough PBR systems disclosed herein undergo photosynthesis, consuming carbon dioxide and producing oxygen as a byproduct, consequently affecting the pH of the system. pH stabilizers serve to stabilize the pH of the system such that the effects on pH of changing carbon dioxide and oxygen concentrations are reduced or eliminated. Exemplary pH stabilizers include calcium carbonate, magnesium, dolomite Ag, Baker's Lime, limestone, magnesium carbonate, potassium hydroxide, sodium hydroxide.

One advantage of the V-trough PBR systems disclosed herein is that there are multiple methods to control the pH of the system, including carbon dioxide flow rate and bubble size, mixing gas flow rate and bubble size, and pH buffers. This allows for an increase in, for example, carbon dioxide flow rate to provide additional carbon source to the biomass to improve productivity without the risk of a detrimental change in pH, since control of pH stabilizers allows precise control of the pH of the system. Likewise, mixing rate of the culture medium can be optimized by adjusting the flow rate and/or bubble size of the gas delivery system without the risk of a detrimental change in pH as discussed above.

Harvesting Aperture

In some embodiments, the V-trough PBR systems disclosed herein further comprise a harvesting aperture for removal of all or a portion of the biomass from the cavity. In some embodiments, the harvesting aperture is located through at least a portion of the distal side wall.

In some embodiments, harvesting is accomplished by automated injection of nutrients, trace elements, pH stabilizers and/or water into the system by the nutrient injection system described below. In some embodiments, harvesting is accomplished by gravity drainage. In further embodiments, harvesting is accomplished by a pumping system. In some embodiments, the pumping system further comprises pumping into a protein skimmer for further harvesting and dewatering.

Nutrient Injection System

In some embodiments, the V-trough PBR systems disclosed herein further comprise injection pumps for the addition of water, nutrients, pH stabilizers, trace elements, pH stabilizers, and/or other components into the system. In illustrative implementations, the nutrient injection system comprises a dosing pump, a tank for supplying nutrients, and an inlet port supplied on one of the walls of the PBR. In some embodiments, the inlet port is supplied through at least a portion of the proximal side wall. In some embodiments, the nutrients are supplied via gravity flow into the V-Trough. In some embodiments where the V-trough system is in the ground, the nutrient holding containers are at ground level and gravity feed into the V-trough. In some embodiments where the V-trough system is above ground, the nutrient holding containers are placed above the level of the V-Trough for gravity feeding nutrients.

In some embodiments, the nutrient injection system provides a means for introducing nutrients, trace elements, water, pH stabilizers, and/or other components into the system. One skilled in the art is familiar with these techniques. In some embodiments, macro and micro nutrients are added to the system at rates determined by the biomass concentration of the system and the available light. Exemplary macronutrients are known to those skilled in the art, and include, but are not limited to, nitrogen, phosphorus, potassium, calcium, magnesium, and sulfur. Exemplary micronutrients are also known to those skilled in the art, and include, but are not limited to, boron, copper, iron chlorine, manganese, molybdenum, and zinc. Exemplary trace elements include, but are not limited to, iron, magnesium, and manganese. In some embodiments, the nutrient injection system feeds from a source containing a mixture of water, nutrients, pH stabilizers and/or trace elements customized to the particular biomass being grown. In further embodiments, the nutrient injection system feeds from multiple sources containing multiple different mixtures. This allows for the separation of elements which might demonstrate undesired reactivity or physical properties, such as chemical reactions, coagulation, and/or precipitation. In some embodiments, the nutrient injection system is controlled such that the addition of water or other liquid, nutrients, pH stabilizers, trace elements, and/or other components can be independently controlled to improve the productivity of the biomass.

In some embodiments, the nutrient injection system comprises an aperture in at least a portion of the proximal side wall. In some embodiments, the nutrient injection system comprises a line comprising perforations, pores, injection points, apertures or orifices. In some embodiments, the nutrient injection system does not extend to the distal side wall. In some embodiments, the nutrient injection system extends less than about half the length of the cavity. In embodiments where the nutrient injection system extends less than about half the length of the cavity and comprises an aperture in at least a portion of the proximal side wall, harvesting through a distally-located harvesting aperture reduces the removal of newly or recently injected nutrients, water or pH buffers during harvest compared to harvesting through a proximally-located harvesting aperture.

Light Source

Many biomaterials used in the V-trough PBR systems disclosed herein require light to grow and produce the desired product. For light-dependent biomaterials, the amount of light received is a function of the surface area of the medium exposed to light, volume of the PBR system, and mixing of the medium within the PBR system. Consequently, a smaller angle of the V-shaped base may result in a greater exposure to light, due to decreased volume and increased mixing. However, a larger angle of the V-shaped base may also result in greater to exposure to light due to increased surface area. The fluid dynamics in the V-trough PBR system creates a mixing of the medium so that the biomaterials are brought to the light for growth.

Materials

The V-trough PBR systems disclosed herein can be made from any suitable materials, of any appropriate thickness. Materials and thickness can depend on the desired application, particular biomaterials, growing medium, location and geographic area for production. In some embodiments, the V-trough PBR systems disclosed herein comprise plastic liners. In some embodiments, the plastic liner is high density polyethylene (HDPE), low density polyethylene (LDPE), polyvinyl chloride (PVC), or ethylene propylene diene monomer (EPDM). In some embodiments, the plastic liner is between about 5 to about 60 mm in thickness. In some embodiments, the liners are semi-rigid. In further embodiments, the liners are completely rigid. In still further embodiments, the liners are flexible. In some embodiments, the liners are capable of being folded, collapsed, or rolled up. In some embodiments, the liners are formed in a desired shape and have resiliency to form that molded shape, but still exhibit overall flexibility.

In some embodiments, the V-trough PBR systems disclosed herein further comprise foam insulation adhered to the outside of the PBR. In some embodiments, the foam insulation provides structural support. In further embodiments, the foam insulation provides insulation which aids in the maintenance of optimum and consistent temperatures required for desired productivity of the biomass. In further embodiments, the V-trough PBR systems disclosed herein are structurally supported by metal, wood, or earth.

In some embodiments, the V-trough PBR systems disclosed herein comprise containers at least partially transparent to light, and/or which are translucent. In further embodiments, the V-trough PBR systems disclosed herein comprise PBRs with open tops to allow light to enter.

Covered V-Trough PBR System

In some embodiments, the V-trough PBR systems disclosed herein further comprise a cover for the cavity. In some embodiments, the cover comprises a greenhouse manifold. In further embodiments, the greenhouse manifold further comprise glazing material. In some embodiments, the glazing material is fabricated from polyethylene, lexan, polycarbonate, clear vinyl, clear polyvinyl chloride, glass or any other material used for covering greenhouses and/or growth chambers, which are known to those skilled in the art. In some embodiments, the cover is affixed to the cavity. In further embodiments, the cover is held to the cavity by gravity. In some embodiments, the cover is made of a flexible material, such that gas evolution can at least partially inflate the cover, creating a positive pressure system.

In embodiments, the cover defines an air volume present in the system. In these embodiments, the air volume affects the amount of solar irradiance, relative and absolute humidities, and ambient temperature of the air in the system. Air volume will depend on several factors, including, but not limited to, geographic location and elevation of the system. The air volume is also dependent on the relationship between the volume of water mass within the covered system, the water temperature, the air temperature outside the covered system and the air temperature inside the covered system. The air volume can be manipulated by altering the height of the covered system to meet the thermal demands of the targeted biomass to be grown, or by adjusting the flexibility of the cover.

In some embodiments, the cover comprises a flexible sheet, corrugated rigid panels, corrugated rigid multi-panels, multi-layer flexible sheets, a combination of corrugated rigid sheets and flexible films, a combination of flexible and/or rigid glazing materials that can be used for covering greenhouse and/or growth, and/or a mixture of the above. In some embodiments, the cover comprises a single layer glazing material and/or a double layer glazing material. In some embodiments, the space between the double layer glazing material comprises air or water which serves as a means of thermal insulation. In some embodiments, the space between the double layer glazing material comprises a chemical constituent that is manipulated via electrical or chemical means to change the insulation and light transmission properties of the cover.

In some embodiments, the cover comprises infrared reflective, infrared absorptive, infrared transmitting materials, and/or a combination of the foregoing for managing heat generated from thermal stress. In further embodiments, the cover comprises wavelength-selective reflective, absorptive, transmitting materials and/or a combination of the foregoing for manipulation of the wavelengths of light that enter the system. The selection of the covering material is dependent on, inter alia, the targeted biomass and geographic location of the system.

In some embodiments, the cover comprises the shape of a loop, A-frame or any other version of greenhouse structures known to those skilled in the art.

In some embodiments, the covered V-trough PBR systems disclosed herein have improved capability to maintain temperature, pH, and concentrations of nutrients, trace elements and/or other components of the system.

In some embodiments, the cover comprises at least one opening or vent.

In some embodiments, the covered V-trough PBR systems disclosed herein provide improved biosecurity by isolating the biomass production system from potential vectors of contamination, such as those that can occur from the exposure to the natural elements. In embodiments where the covered PBR system is a positive pressure system, contaminants such as dust are preventing from entering the system through apertures or vents.

Other Features

In some embodiments, the V-trough PBR systems disclosed herein further comprise a harvesting aperture. In some embodiments, the harvesting aperture is disposed through at least a portion of the distal side wall.

In some embodiments, the V-trough PBR systems disclosed herein are level along their lengths, i.e. having a slope of 0. In further embodiments, the systems are off-level or sloped along their lengths to increase the ease of harvesting the desired product at the low end, to drive biomass from one end to a harvesting end, to assure mixing and turnover within the system, to skim the top of the culture out of the system, or to allow spill over for ease of harvesting. In some embodiments, the slope or leveling of the system is modified by grading of the land on which the system sits, or by modifying the dimensions of the structural support on which the system sits. In some embodiments, the offset of one end of the system to the other is between about 0.5 and about 6 inches. In some embodiments, a system comprising a cavity length of about 15 feet comprises an offset of about 0.5 inches. In further embodiments, a system comprising a cavity length of about 10 feet comprises an offset of about 4 to about 6 inches.

In some embodiments, the V-trough PBR systems disclosed herein further comprise temperature and/or pH sensors.

In some embodiments, the V-trough PBR systems disclosed herein further comprise controls to add water, nutrients, pH stabilizers, and further biomass to the system. In some embodiments, these controls are automated in conjunction with sensors such that productivity is optimized and held roughly constant.

In some embodiments, the V-trough PBR systems disclosed herein further comprise cooling and/or heating means. In some embodiments, the cooling and/or heating means comprise at least one heat exchanger. In further embodiments, the cooling and/or heating means comprise pan and fan evaporative cooling systems. Such systems are known to those of skill in the art, and are described in Bucklin, et al., *Fan and Pad Greenhouse Evaporative Cooling Systems*, Univ. of Fla. Dept. of Agric. and Biological Eng'g, Fla. Coop. Extension Serv., Inst. of Food and Agric. Sci. Circular 1135, December 1993, available at http://edis.ifas.ufl.edu/ae069 or http://edis.ifas.ufl.edu/pdffiles/AE/AE06900.pdf, which is incorporated herein by reference in its entirety. In some embodiments, the cooling and/or heating means comprise cooling by water mist sprayed to cool the air surrounding the systems. In some embodiments where the V-trough PBR systems disclosed herein are in an enclosed structure, such as a greenhouse or the covered V-trough PBR systems disclosed herein, further cooling is achieved by natural or mechanical ventilation of the structure. In some embodiments, use of the preceding heating and/or cooling means improves and reduces the operational costs of maintaining the temperature of the culture medium in the systems disclosed herein. In some embodiments, the cooling and/or heating means comprise heating systems and/or covering materials which retain heat loss via black body radiation. In further embodiments, the V cooling and/or heating means comprise geothermal heating and/or cooling, subterranean heating and/or cooling, gas burners, air conditioners, waste heating and/or cooling from industrial sources, and/or a combination of the foregoing. In some embodiments, a combination of foam structural insulation and covering materials is utilized for maintaining diurnal temperature fluctuation.

In some embodiments, the V-trough PBR systems disclosed herein are stand-alone units. In further embodiments, the systems are dug into the ground for added stability and improved insulation for maintaining optimum and consistent temperatures required for desired productivity of the biomass.

In some embodiments, the V-trough PBR systems disclosed herein further comprise a drain for harvesting biomaterials. In some embodiments, the drain is opposite controls such that as water, nutrients, pH stabilizers and biomass are added to the system, water is forced out of the drain. In some embodiments, the drain is on the proximal wall, while the controls are on the distal wall. In further embodiments, the drain is on the distal wall, while the controls are on the proximal wall.

In some embodiments, airlift technology is used to pump water into or out of the system via the gas and carbon dioxide delivery systems. In further embodiments, airlift technology is used to pump water into or out of the system via a separate system. As known by those skilled in the art, airlift technology is a process used in aquaculture for moving water via air. The concept behind the process is to inject air into water at a point in a pipe and/or vessel where the buoyancy of the bubble lifts the water to the desired area. The rate of flow is determined by the air flow into the vessel, the density of the air or gas used, the density of the water, and the diameter or size of the vessel. Air lift pumping can be more energy efficient and economical when compared to conventional means of pumping such as by centrifugal pumps.

In some embodiments, the V-trough PBR systems disclosed herein breaks down into small pieces for efficient shipping. In some embodiments, the system is a turnkey system that can be delivered to a site, set up, and retrofitted with necessary components. In some embodiments, the V-trough PBR systems disclosed herein comprise a structural support, and a first liner disposed on top of the structural support which comprises the cavity of the system. In some embodiments, the support structure is foam. In some embodiments, the support structure comprises stackable pieces which can be broken down to facilitate shipment. In some embodiments, the support structure comprises foam blocks. In further embodiments, the system further comprises a second liner which at least partially contains the support structure. In some embodiments, the second liner helps maintain the shape of the support structure. In some embodiments, the first and second liners are secured to one another. In some embodiments, the liners are secured by friction. In further embodiments, the liners are secured by mechanical means. In still further embodiments, the liners are secured by chemical means. In some embodiments, the liners are secured by clamps or adhesives. In some embodiments, the liners are secured by heating. In some embodiments, the support structure is broken down and stacked, and the first and/or second liners are folded, collapsed, or rolled up to facilitate shipment. The ability to break down and fold, collapse or roll up the separate components of the V-trough PBR systems disclosed herein facilitates more efficient shipment by conventional means, where the structural support can be assembled onsite, either by itself or at least partially contained within the unrolled, uncollapsed or unfolded second liner to help maintain its shape, and the first liner placed on the support to form the cavity.

In some embodiments, the V-trough PBR systems disclosed herein further comprise light reflecting means which increase the amount of light directed into the system.

In some embodiments, the V-trough PBR systems disclosed herein further comprise gravity lines. In some embodiments, the gravity lines are used for harvesting biomass or introducing water, nutrients, trace elements and/or pH stabilizers without the use of a pump. In the foregoing embodiments, biomass can be harvested from, or water, nutrients, trace elements pH stabilizers and/or other components can be introduced into the culture medium by varying the elevation of the gravity line and/or fluid source with respect to the PBR system.

Automated Sensor and Control Systems

Some embodiments of the V-trough PBR systems disclosed herein further comprise a sensor and control system for maintaining and modifying conditions within the V-trough PBR system. Such systems are known by those skilled in the art. In some embodiments, the sensor and control system monitors the conditions in the PBR system and controls various components of the PBR system via computer, data logger, programmable logic control, any other type of real time monitoring and control system, or any combination thereof. In some embodiments, the sensor and control systems disclosed herein comprise at least one sensor and/or at least one control.

In some embodiments, the sensor and control system comprises a data logging system that is equipped with sensors and controls which monitor and control various aspects of the V-trough PBR systems disclosed herein. In some embodiments, the data logging system comprises a National Instruments, Campbell Scientific, and/or Allen-Bradley product, or a combination of the foregoing.

In some embodiments of the V-trough PBR systems disclosed herein, the sensors disclosed herein comprise temperature, carbon dioxide, ozone, dissolved oxygen, light, relative humidity, air speed, pH, chlorophyll A, phycobilins, turbidity, optical density and/or electrical conductivity sensors, or any combination of the foregoing. In some embodiments, the sensors comprise Campbell Scientific, Honeywell, YSI, National Instruments, and/or Hanna Instruments products, or a combination of the foregoing. In some embodiments, real-time feedback from the sensors is analyzed by software uploaded to the data logger equipment. In some embodiments, real-time feedback from the sensors is processed and control systems are adjusted according to set points and applications set forth in the software program. In some embodiments, environmental set points are determined with reference for favorable growing conditions of the targeted biomass. In some embodiments, the senor systems are wireless systems, reducing the need for wires and other materials.

In some embodiments, the sensor and control system is run in a continuous or semi-continuous mode. In further embodiments, the sensor and control system is run to adjust and maintain selected parameters within predetermined limits to provide a beneficial environment for the selected biomass. In some embodiments, the sensor and control system controls the amount of light and standing biomass concentration in the system to improve the productivity of the system.

In some embodiments, the sensors disclosed herein monitor air temperature and humidity and the controls disclosed herein adjust these properties using cooling and/or heating means. In some embodiments, the sensors disclosed herein monitor the temperature of the culture medium and the controls disclosed herein control the heating and/or cooling system to maintain and/or control the temperature.

In some embodiments where the V-trough PBR system is covered, the sensors disclosed herein monitor the carbon dioxide and dissolved oxygen in the air space to determine the amount of gas that leaves the system.

In some embodiments, the sensors disclosed herein monitor the pH of the culture medium and the controls disclosed herein maintain and/or adjust desired pH thresholds of the culture medium for the targeted biomass. In some embodiments, the controls disclosed herein maintain or adjust desired pH thresholds by stabilizing or adjusting the pH of the culture medium by adjusting or maintaining a combination of the flow rate and bubble size of gas and carbon dioxide introduced into the system, the addition of pH stabilizers, and/or other factors, or a combination of the foregoing.

In some embodiments, the sensors disclosed herein monitor chlorophyll A and/or phycobilin concentration in the culture medium to determine the amount of biomass in the system. Chlorophyll A and phycobilins are photo-harvesting pigments in algae and cyanobacteria. If cyanobacteria is not the biomass that is targeted for production, then the phycobilin concentration can be used to determine the amount of cyanobacteria contamination within the system.

In some embodiments, the sensors disclosed herein monitor the amount of light entering the PBR system, and the controls disclosed herein adjust or maintain the harvest rate to compensate for the amount of light that is entering the system. In some embodiments, light sensors and controls enable the operation of the PBR system at a desired productivity as determined by the light level.

In some embodiments, the sensors disclosed herein comprise one or more turbidity sensors, chlorophyll A sensors and/or optical density sensors. In these embodiments, the foregoing sensors are utilized individually or in conjunction with one another to measure real-time biomass concentrations in the system. In some embodiments, the controls disclosed herein utilize the real-time biomass concentration measurements determined by the sensors disclosed herein to control the harvest rate, nutrient injection rate, contamination rate, or a combination of the foregoing. In these embodiments, the controls disclosed herein initiate nutrient injection and/or harvesting depending on the productivity in the system. In some embodiments, electrical conductivity sensors measure the salt content of the water, and the controls disclosed herein provide salinity and fertilizer salts in the system to adjust to the desired concentration. In some embodiments, the controls disclosed herein maintain or adjust the nutrient injection rate based on electrical conductivity measurements made by the sensors disclosed herein. In these embodiments, a desired or target electrical conductivity level is determined relative to the targeted biomass for production.

In some embodiments, sensors disclosed herein measure contamination of the medium by the productivity rate of the PBR system and the difference between the turbidity and chlorophyll A concentration in the system. In some embodiments, contamination is monitored by one or more phycobilin sensors, where the targeted biomass is not a cyanobacteria. In some embodiments, the controls disclosed herein apply contamination treatments the PBR system to maintain desired productivity by killing, inhibiting or reducing the concentration of potential contaminants that inhibit or effect biomass productivity. In some embodiments, ozone is applied to the system to prevent contamination. In further embodiments, ozone is applied prophylactically, to prevent contamination rates reaching detrimental levels in the culture. The amount and timing of the ozone application for sterilization of the culture is determined by the contaminant in question. In some embodiments, ozone is applied at levels between about 0.5 and about 1 mg/L for sterilizing viable cultures without effecting the targeted biomass. In some embodiments, the sensor and control system comprises an ozone sensor and control for ozone application, wherein ozone is adjusted and maintained within a predetermined range to prevent contamination rates from reaching detrimental levels in the culture. In some embodiments, ozone is adjusted and maintained between about 0.5 and about 1 mg/L of culture. In some embodiments, ozone levels between about 0.5 and about 1 mg/L are sufficient to kill or prevent the growth of contaminants, but will not harm biomaterials such as Nannochloropsis.

The Figures that follow demonstrate how the full spectrum of solar radiation can be used by splitting the full spectrum into selected and non-selected wavelengths of radiation.

FIG. 1 shows an illustrative embodiment of the V-trough PBR systems disclosed herein, where substantially V-shaped base 100 (comprising two base walls 125 with sloped portions 135 and substantially vertical portions 140), proximal side wall 130 and distal side wall 160 define cavity 145. FIG. 1 also shows sloped portions 135 of base walls 125 meeting proximate to axis 190, along which gas delivery system 170 lies, which base walls further define interior angle 195. FIG. 1 further shows two carbon dioxide delivery systems 150 disposed parallel to axis 190 and gas delivery system 170. FIG. 1 still further shows carbon dioxide delivery systems 150 comprising carbon dioxide terminals 120 through proximal side wall 130, and gas delivery system 170 comprising gas delivery terminal 110 also through proximal side wall 130. FIG. 1 also shows that the system further comprises apertures 180 through proximal side wall 130, which may be apertures for a nutrient injection system.

Figure 2:
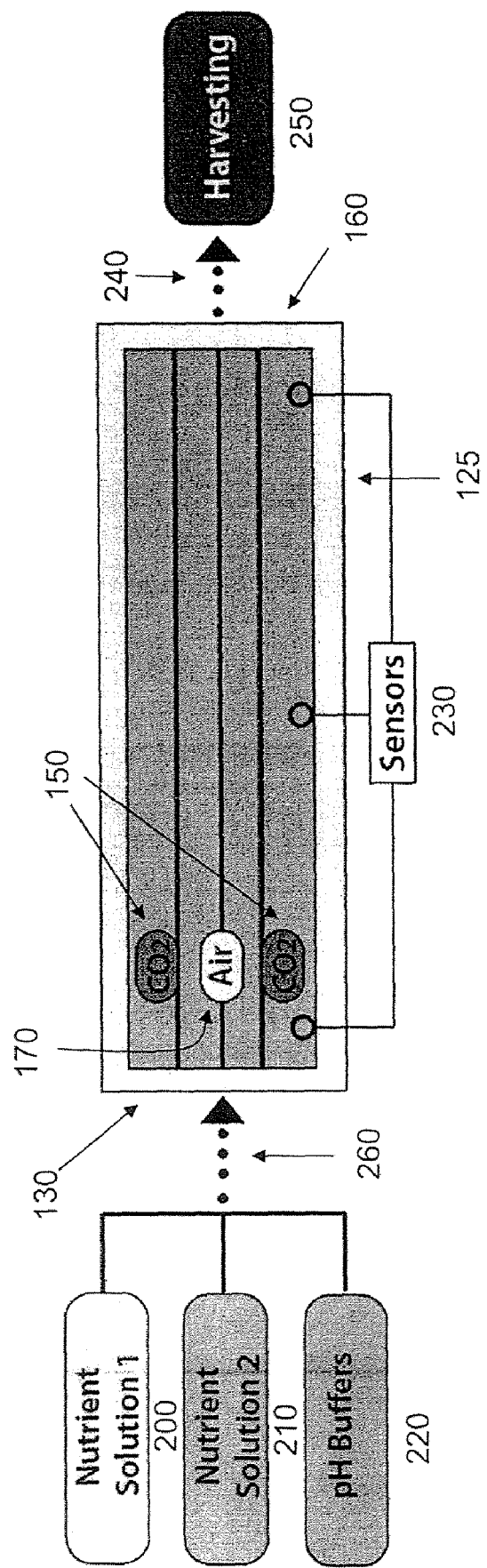
FIG. 2 shows a bird's eye view of an additional illustrative embodiment of the V-trough PBR systems disclosed herein.

FIG. 2 shows another illustrative embodiment of the V-trough PBR systems disclosed herein, where nutrient injection system 260 feeds from nutrient solutions 200 and 210, as well as pH stabilizer 220 to inject these components through proximal side wall 130. FIG. 2 shows that the system further comprises gas delivery system 170, carbon dioxide delivery systems 150, sensors 230 (distributed at three different positions along base wall 125), and a harvesting aperture 240 trough distal side wall 160, feeding to harvesting receptacle 250.

Figure 3:
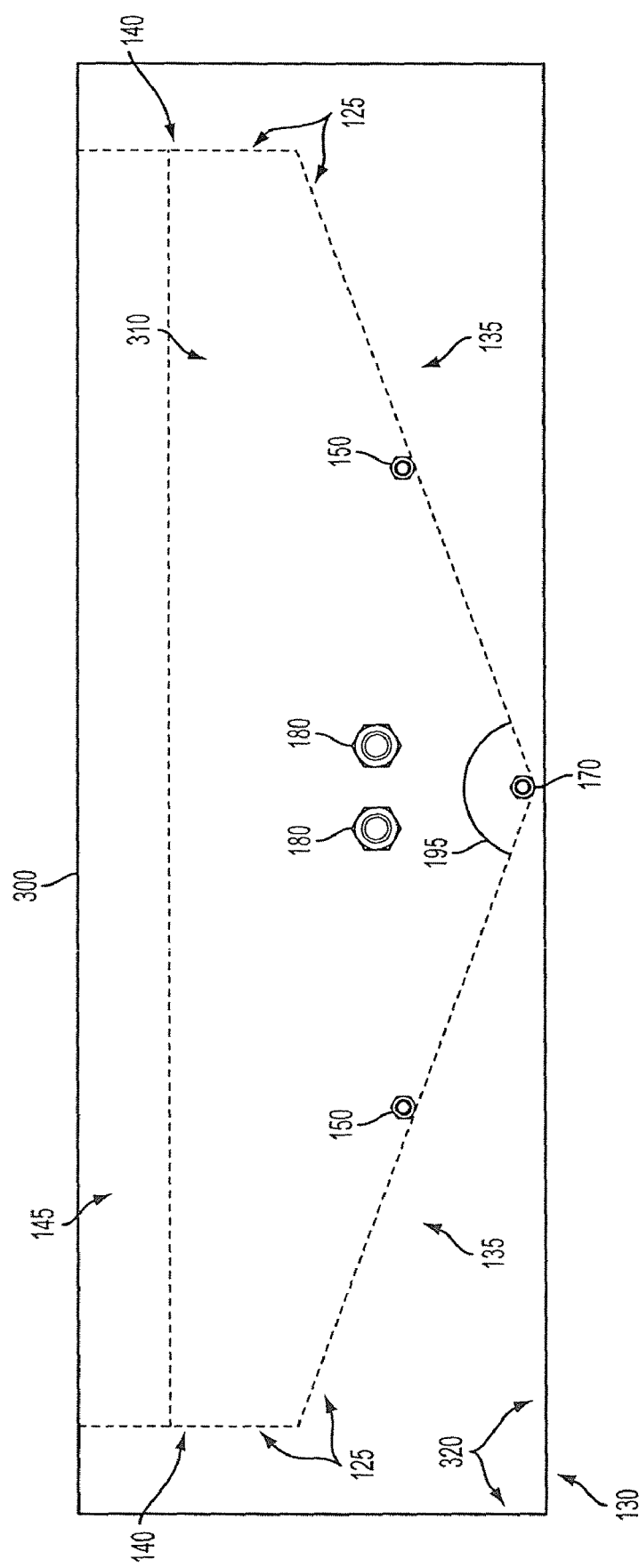
FIG. 3 shows an end-on view of the proximal side wall of an illustrative embodiment of the V-trough PBR systems disclosed herein.

FIG. 3 shows another illustrative embodiment of the V-trough PBR systems disclosed herein, looking end on at proximal side wall 130, where sloped portions 135 and substantially vertical portions 140 of base walls 125, proximal side wall 130 and the distal side wall (not pictured) define cavity 145. FIG. 3 also shows sloped portions 135 of base walls 125, which define interior angle 195, cover 300, and culture medium 310. FIG. 3 also shows carbon dioxide delivery systems 150, separated from gas delivery system 170, and nutrient injection apertures 180 through proximal side wall 130. Further, FIG. 3 shows support structure 320.

Figure 4:
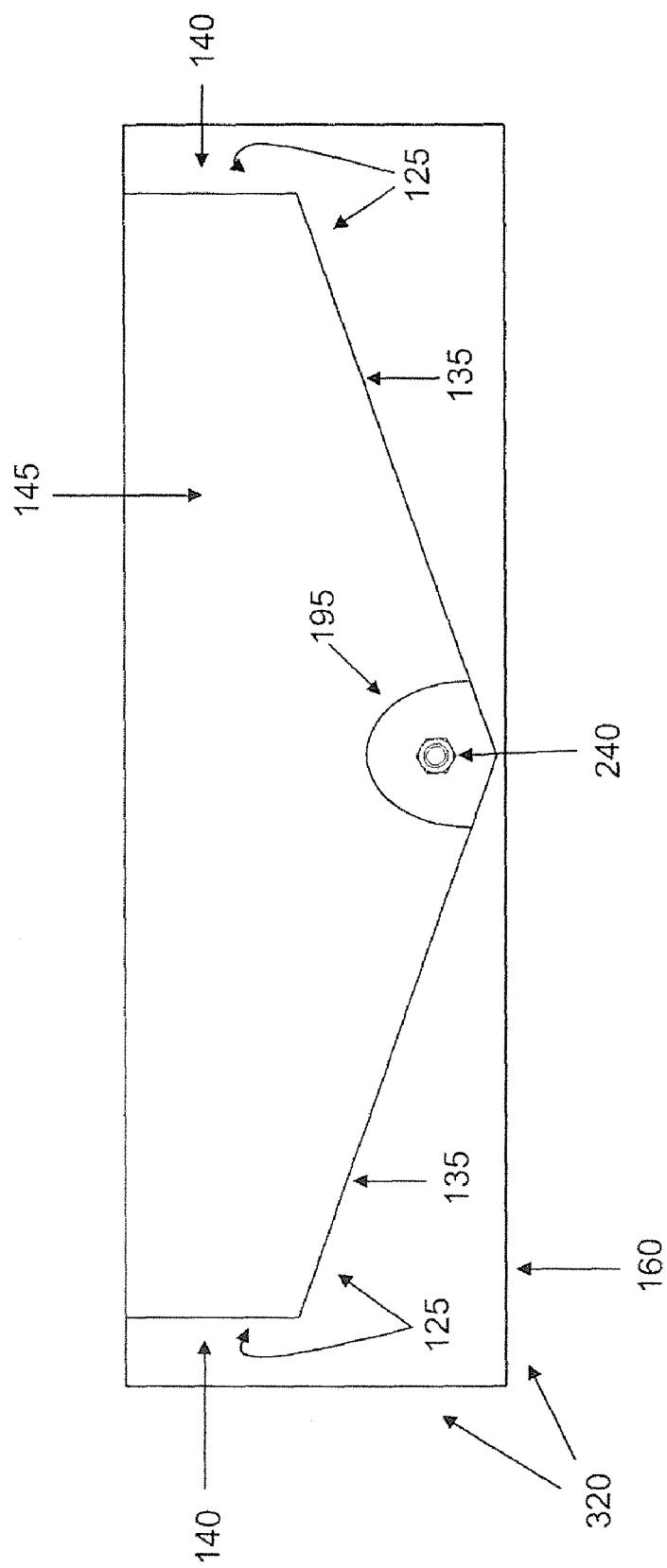
FIG. 4 shows an end-on view of the distal side wall of an illustrative embodiment of the V-trough PBR systems disclosed herein.

FIG. 4 shows another illustrative embodiment of the V-trough PBR systems disclosed herein, looking end on at distal side wall 160, where sloped portions 135 and substantially vertical portions 140 of base walls 125, the proximal side wall (not pictured) and distal side wall 160 define cavity 145. FIG. 4 further shows sloped portions 135 of base walls 125 defining interior angle 195, and also shows harvesting aperture 240 through distal side wall 160. Further, FIG. 4 shows support structure 320.

Figure 5:
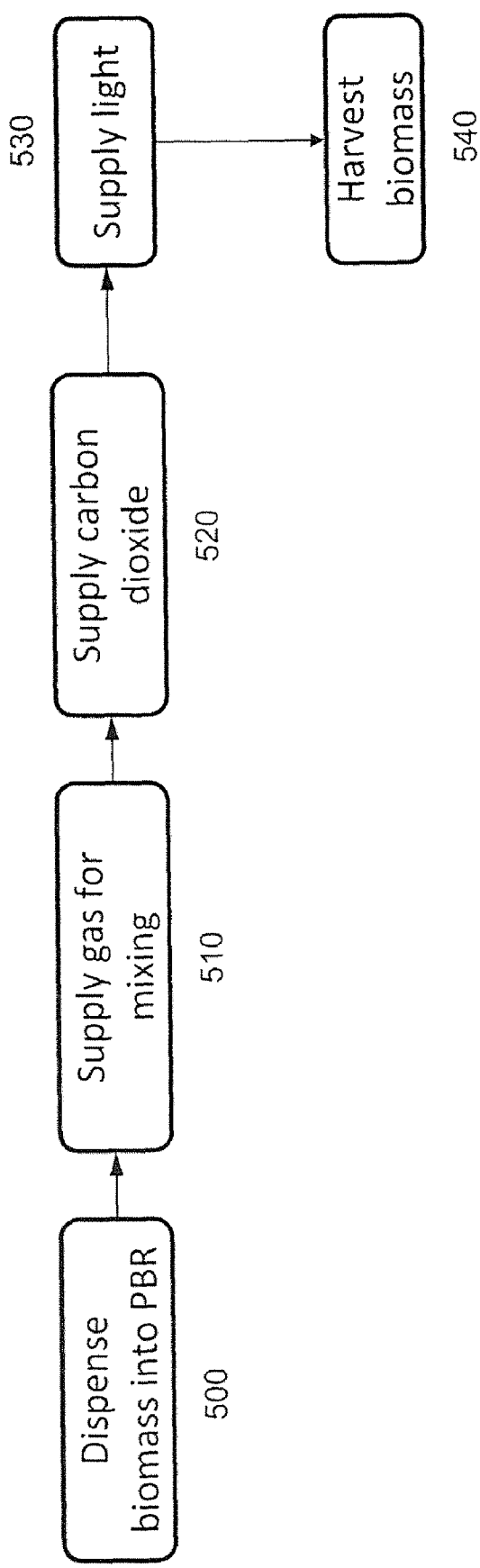
FIG. 5 shows a flowchart of an illustrative embodiment of the method for growing a biomass using the V-trough PBR systems disclosed herein.

FIG. 5 shows a flowchart of an illustrative embodiment of the method for growing a biomass using the V-trough PBR systems disclosed herein wherein biomass is dispensed into a PBR 500, gas is supplied for mixing 510 via a gas delivery system, carbon dioxide is supplied 520 through a carbon dioxide delivery system, light is delivered 530 for biomass growth, and the biomass is harvested 540.

Figure 6:
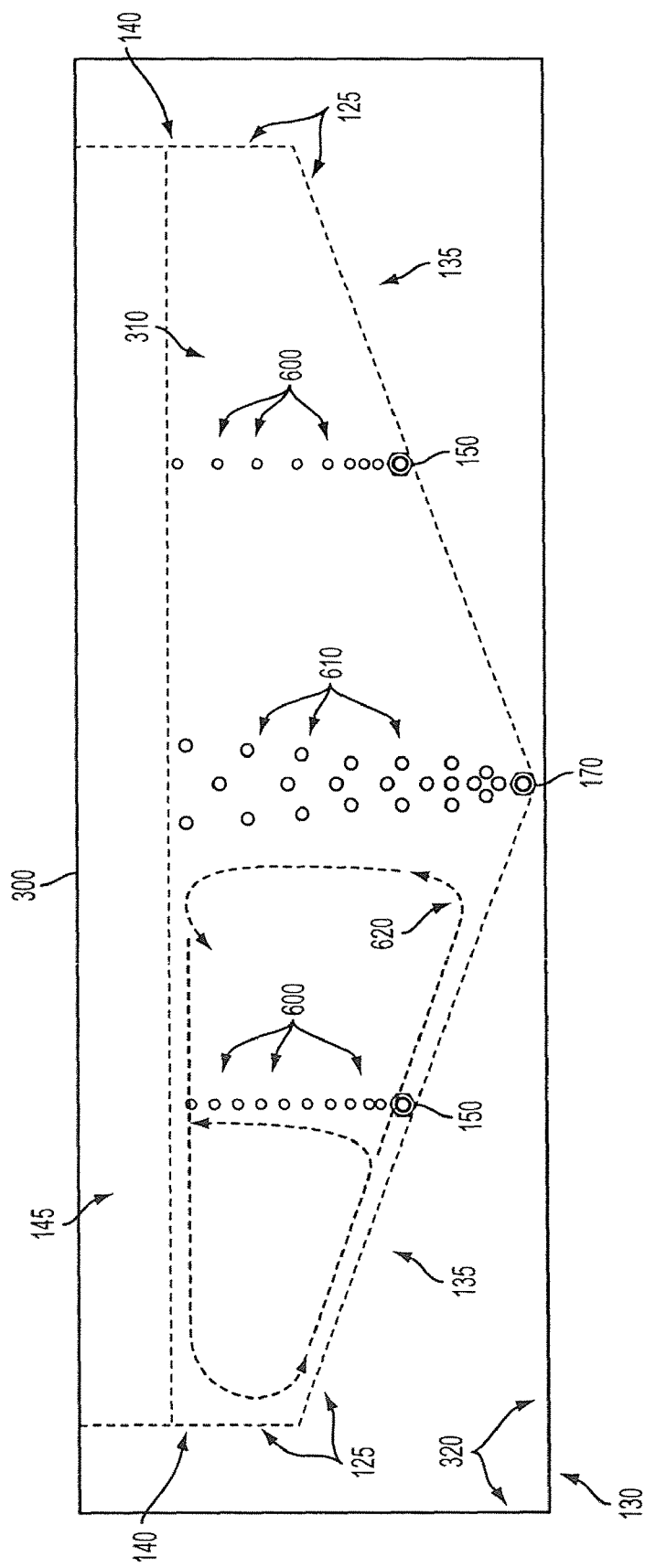
FIG. 6 shows an end-on view of the proximal side wall of an illustrative embodiment of the V-trough PBR systems disclosed herein.

FIG. 6 shows an end-on view of the proximal side wall of an illustrative embodiment of the V-trough PBR systems disclosed herein which illustrates the circulation pattern 620 on one side of the system (circulation pattern on the other side not shown). FIG. 6 shows gas bubbles 610 as the major contributor to circulation, with carbon dioxide bubbles 600 additionally contributing, but less significantly.

FIG. 7 shows an exploded aspected view of an illustrative embodiment of the V-trough PBR systems disclosed herein, where disassembled system comprises a molded liner 700 defining cavity 145, which is ready for assembly with proximal side wall 130, distal side wall 160 and base walls 125.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of producing a biomass comprising:
   a) dispensing a biomass culture medium in a photobioreactor, the photobioreactor comprising:
      i) a cavity defined by:
         1) a substantially V-shaped base comprising two base walls, said base walls meeting proximate to an axis defining an interior angle, each base wall comprising:
            A) a sloped portion and a substantially vertical portion;
            B) a proximal end and a distal end; and
            C) a length extending along said axis and a width extending perpendicular to said axis;
         2) a proximal side wall adjacent to said proximal end;
         3) a distal side wall adjacent to said distal end;
      ii) at least one gas delivery system disposed within said cavity and extending parallel to said axis; and
      iii) at least one carbon dioxide delivery system disposed within said cavity and extending parallel to said axis;
   b) supplying a gas through said gas delivery system, producing bubbles having diameters between about 1 and about 3 mm; and
   c) supplying carbon dioxide through said carbon dioxide delivery system, producing bubbles having diameters between about 0.001 and about 500 microns.

2. The method of claim 1, further comprising controlling a flow rate of at least one of said gas through said gas delivery system and said carbon dioxide through said carbon dioxide delivery system, wherein solids are substantially prevented from settling by flow of at least one of said gas exiting said gas delivery system and said carbon dioxide exiting said carbon dioxide delivery system.

3. The method of claim 1, said photobioreactor further comprising an ozone sensor and control system; and
   said method further comprising operating said ozone sensor and control system such that ozone levels in said culture medium are maintained between about 0.5 and about 1 mg/mL;
   wherein said ozone sensor and control system comprises at least one ozone sensor disposed so as to measure ozone within said culture medium and an ozone delivery system for delivering ozone to said culture medium; and
   wherein said ozone levels are adjusted by said ozone delivery system based on information from said ozone sensor.

4. The method of claim 1, said photobioreactor further comprising a temperature sensor and control system; and
   said method further comprising operating said temperature sensor and control system to maintain the temperature of said culture medium in an optimal range for the targeted biomass;
   wherein said temperature sensor and control system comprises at least one temperature sensor disposed so as to measure the temperature of said culture medium and a temperature control system for controlling the temperature of said culture medium; and
   wherein said temperature of said culture medium is adjusted or maintained by said temperature control system based on information from said temperature sensor.

5. The method of claim 4, wherein said photobioreactor further comprises a cover, the cover cooperating with the walls defining the cavity to contain an atmosphere.

6. The method of claim 5, wherein said temperature sensor and control system further comprises at least one relative humidity sensor for measuring the relative humidity of said atmosphere, at least one gas speed sensor for measuring a flow of a gas of said atmosphere within said cavity, and a gas speed control system; and wherein the gas speed is adjusted by said gas speed control system based on information from said relative humidity sensor and said gas speed sensor to maintain or adjust said temperature.

7. The method of claim 1, further comprising harvesting at least a portion of said biomass.

8. The method of claim 7, said photobioreactor further comprising a light sensor and control system, wherein said light sensor and control system comprises at least one light sensor for measuring light entering said cavity and a light control system for controlling the light entering said cavity.

9. The method of claim 8, wherein said light sensor and control system measures and controls at least one of the intensity, propagation direction, frequency, wavelength spectrum, and polarization of said light.

10. The method of claim 9, said method further comprising adjusting or maintaining a rate of said harvesting based on information from said light sensor.

11. The method of claim 9, said method further comprising operating said light sensor and control system such that at least one of the intensity, propagation direction, frequency, wavelength and polarization of light entering said cavity is adjusted or maintained based on a rate of said harvesting.

12. The method of claim 1, said photobioreactor further comprising a pH sensor and control system; and said method further comprising operating said pH sensor and control system to maintain the pH of said culture medium in an optimal range for the targeted biomass;

wherein said pH sensor and control system comprises at least one pH sensor disposed so as to measure the pH of said culture medium and a pH control system for controlling the pH of said culture medium; and wherein said pH of said culture medium is adjusted or maintained by said pH control system based on information from said pH sensor.

13. The method of claim 12, wherein said pH sensor and control system further comprises one or more carbon dioxide sensors; and wherein an amount of carbon dioxide supplied to said culture medium by said carbon dioxide supply system is adjusted based on information from said pH sensor and said carbon dioxide sensor to adjust the pH of said culture medium.

14. The method of claim 12, wherein said pH sensor and control system further comprises one or more dissolved oxygen sensors; and wherein an amount of oxygen supplied to said culture medium is adjusted based on information from said pH sensor and said dissolved oxygen sensors.

15. The method of claim 1, said photobioreactor further comprising a productivity sensor and control system; and said method further comprising operating said productivity sensor and control system such that the productivity of said culture medium is optimized and held roughly constant;

wherein said productivity sensor and control system comprises at least one biomass concentration sensor to measure the concentration of biomass in said culture medium and a biomass concentration control system configured to adjust said concentration of biomass in said culture medium; and wherein said concentration of said biomass is adjusted or maintained by said biomass concentration control system based on information from said biomass concentration sensor.

16. The method of claim 15, wherein adjusting said concentration of said biomass includes at least one of adding or removing biomass, adding or removing water, adding or removing nutrients, adding or removing pH stabilizers, or combinations thereof; and wherein said biomass concentration sensor includes at least one of turbidity sensors, electrical conductivity sensors, phycobilin sensors, chlorophyll A sensors, optical density sensors, or combinations thereof.

* * * * *